United States Patent [19]

Wu

[11] Patent Number: 5,595,743
[45] Date of Patent: Jan. 21, 1997

[54] PREPARATION OF HERBAL MEDICINES BY USING A MULTI-ENZYME SYSTEM, HERBAL MEDICINES PREPARED AND THEIR USES

[76] Inventor: Wencai Wu, 11 Ganggou, Haidian District, Beijing 100080, China

[21] Appl. No.: 359,693

[22] Filed: Dec. 20, 1994

[30] Foreign Application Priority Data

Dec. 21, 1993 [CN] China .............................. 93 1 20926.9

[51] Int. Cl.$^6$ .......................... A61K 35/78; A61K 38/46; A61K 38/47; A61K 38/48
[52] U.S. Cl. .................. 424/195.1; 424/94.6; 424/94.61; 424/94.62; 424/94.63; 424/94.64; 424/94.65; 424/94.66; 424/94.67; 514/866
[58] Field of Search .................... 424/195.1, 94.6–94.67; 514/866

[56] References Cited

U.S. PATENT DOCUMENTS 5,202,122  4/1993  Graves et al. ........................ 424/195.1

*Primary Examiner*—John W. Rollins
*Attorney, Agent, or Firm*—Sughrue, Mion, Zinn, Macpeak & Seas

[57] ABSTRACT

This invention relates to a process for preparing a herbal medicine by using a multi-enzyme to hydrolyze raw materials. The multi-enzyme system comprises cellulases, proteases, amylases, lipases and lysozyme, and may further comprise a supplementary enzyme, and a herbal medicine prepared by the process of the invention.

17 Claims, No Drawings

PREPARATION OF HERBAL MEDICINES BY USING A MULTI-ENZYME SYSTEM, HERBAL MEDICINES PREPARED AND THEIR USES

This invention relates to a process of preparing herbal medicines by using a multi-enzyme system and relates to herbal medicines made by the process and their pharmaceutical uses.

BACKGROUND OF THE INVENTION

Herbal medicines have been used for treating various diseases in various countries for a very long period of time. The preparations of herbal medicines have been developed in years. A typical traditional method for example, used in China is a physical preparation method, such as, stirring-baking, decocting and parching.

In recent decades, a chemical purification method has been developed for preparing herbal medicines in which active ingredients of raw material are extracted and purified. Without the balance of other ingredients, the toxicity and side effects are increased in the herbal medicines prepared by the chemical purification method.

A new method of preparing herbal medicines is desired by which herbal medicines have quicker therapeutical effect and lower toxicity and side effects.

SUMMARY OF THE INVENTION

One of the objections of the present invention is to provide a process for preparing herbal medicines in which a multi-enzyme system is used in treating raw materials.

Another objection of the present invention is to provide new herbal medicines prepared by using a multi-enzyme system which may be used in treating various diseases.

Another objection of the present invention is to provide new herbal medicines which have better solubility and higher therapeutical effect.

Another objection of the present invention is to provide a process for preparing herbal medicine at lower costs in which a multi-enzyme system is employed to increase the solubility of the herbal medicines by transferring large molecular materials into low molecular materials.

Further and other objections of the present invention may be illustrated from the following description of the present invention in detail.

According to the present invention, a process of preparing a herbal medicine comprises the steps of forming a mash from raw material, first finely grinding the mash so that the size of the suspension particles of the said mash is less than 50 μm, treating the ground material with biological enzymes to promote the hydrolysis of the said material in which the biological enzymes form a multi-enzyme system comprising cellulases, proteases, amylases, lipases and lysozymes, and sterilizing the enzymatic hydrolysis material.

The present invention relates also to the herbal medicines prepared by the above mentioned process and uses of these herbal medicines in the treatment of human and/or animal diseases.

There are many advantages as follows by using multi-enzyme system to process herbal medicines preparations.

1. The solubility of original medicines can be dramatically improved and increased from 4–5% in traditional method to 65–99%;

2. The ratio of dissolution of effective medical composition of original medicine can greatly be increased due to the reinforcing treatment of solubility. It can be increased to nearly 100%, which facilitates processing and purification.

3. That high molecular materials, such as cellulose, protein, starch etc. can be conversed into oligosaccharide, oligopepitde, and saponin which can be very easily absorbed by human body, leads to inductive absorption. As a result, the absorptivity of effective medical compositions can be increased to nearly 100% from 10–60% of traditional method. The therapeutical effect is prominent and the effectual time is greatly shortened to be the same as that of western medicines.

4. Oligosaccharide, oligopeptide and saponin have effects in regulating human body's immunity and endocrine functions and can be used for immunity therapy in modem medicines. Therefore, a number of oligosaccharides and oligopeptides, existing in the Chinese herbal medicine preparations by the process of the present invention, can reinforce the effect, so that the effective dosages of Chinese herbal medicines may be reduced to 1/10–1/200 of that in the traditional method.

5. During the process of production, conventional techniques in high temperature treatment, such as stirring-baking, parching and decocting have been totally discarded. The processing is carried out under mild condition with normal temperature, which avoids color deteriorated change on account of oxidation and etc., and makes preparations mainly keep the color of original medicines. In addition, the outward appearance of products can be accepted easily.

6. It is the present invention that makes the form of Chinese herbal medicine wonderful, such as, small dosage, good quality and fine processing, without boorish outward appearance.

7. The process of the present invention has no selectivity to raw materials, which adapts to any medicines from animal and plant resources.

8. The medicines prepared by the process of the present invention, being rich in bio-active materials, can effectively promote the reparation of ribose nucleic acids (RNA) and deoxyribonucleic acids (DNA). That is, enzymes secreted from cells can decompose diseased ribose nucleic acids and deoxyribonucleic acids, at the same time, can promote the synthesis of normal ribose nucleic acids and deoxyribonucleic acid and facilitate the synthetic speed (it is about 2–5 times faster than that under usual conditions). Neogenesic cells can clear the foci as well as repair the structure and function of diseased tissues. In such a way, they can provide effective therapy to those diseases, which can not be cured by traditional Chinese and western medicines, such as diabetes mellitus, hyperosteogeny, oncosis, rheumatic/rheumatoid arthritis, diseased connective tissue and collagen, psoriasis etc. At the same time, the herbal medicines of the present invention have a function of systematic therapy. That is to say that one particular herbal medicine can be used for treating all diseases in a particular anatomical system.

9. When the medicines prepared by the process are used in therapy, its methods of medical caring completely follow the theories of modem molecular medicine and cell medicine. It is scientifically and practically better than traditional ways, and can greatly increase the curative rate.

DETAILED DESCRIPTION OF INVENTION

According to the present invention, a process of preparing herbal medicines comprises treating a raw material with biological enzyme system that contains multi-biological enzymes to promote the hydrolysis of the said raw material. Before treated with the multi-enzyme system, the raw material is pre-treated in the following steps.

First, the raw material is crushed or beaten to form a mash by conventional processes, such as mechanical crushing or beating process. The particles of the crushed or beaten raw material are small, making it easier to perform the next steps. The average size of the said particles is about 600 meshes to about 2000 meshes. During the formation of the mash, the crushed or beaten raw material may also be soaked. In some instances, the soaked step may be taken place before the raw material is crushed or beaten, particularly when the raw material is drier. Generally speaking, moisture in the raw material is gradually lost during storing, and the longer the material is stored, the more moisture will be lost. Therefore, when raw material has less than 50% of moisture/content, an adequate amount of water is added during the step of soaking in order to maintain the moisture content of the cracked raw material higher than 50%, preferably between 75% to 80%. The time of soaking varies according to the degree of freshness of the raw material. The fresher the material is, the shorter it will be pre-soaked. Normally, the soaking time is 15 minutes to 36 hours.

The soaked material is then subject to first fine grinding. The size of the suspended particles of the finely ground material is less than 50µm.

The ground mash is then treated with biological enzyme to promote the hydrolysis of the material while stirred. The biological enzyme used in the present invention is multi-enzyme system that comprises cellulases, proteases, amylases, lipases and lysozymes. In addition, according to the type of raw materials to be treated the multi-enzyme system may further comprises one or more of supplementary enzymes, such as hemicellulases, pectases, glucase peptidases, or peptichainases etc.

During the enzyme treatment, the activity. unit of the enzyme used is 20,000–10,000,000 IU/g and the specific activity concentration is about 1 to 1000 IU/g substrate. With the increase in the loss of moisture in the raw material, the specific activity concentration of the enzyme system used is slightly increase. Generally, the temperature of enzyme hydrolysis is about 20°–80° C. and the time of enzyme hydrolysis is from about 5 minutes to about 144 hours.

The enzyme-treated material may be subject to second finely grinding to give an average particle size of less than 5 µm in some cases.

After the second finely grinding, the enzyme-treated material may or may not be filtered to eliminate the residues which depends on the desired form of a herbal medicine produced. During the filtering step, the material is filtered so that the particles of the filtered material are of the desired average sizes.

In order to enable the product to have good stability and maintain maximum biologically active material, the enzyme-treated material, filtered or not filtered, is then sterilized. The sterilization of the present invention is carried out under a temperature about 50° C. or below.

The sterilizing step in the present invention involves using ultrafiltration or ultrasonic sterilizing method. Or both ultrofiltration and ultrasonic method are used. The ultrasonic sterilizing method comprises killing the bacterium and enzyme and sterilizing the material while it is flowing through an ultrasonication apparatus. The frequency of the ultrasonic waves suitable for use in the present invention is about 20–100 KHz, the power density is over 100 W/cm$^2$, and the flow speed is about 1–25 m/s.

According to the present invention, the multi-enzyme system used in the process comprises, by weight, 5–75% of cellulases, 5 to 50% of proteases, 5 to 50% of amylases, 1 to 20% of lipases, and 1 to 15% of lysozymes. Depending on the raw materials to be processed, the multi-enzyme system may further comprise one or more supplementary enzymes, for example, 0 to 15% of hemicellulases, 0 to 30% of pectases; 0 to 10% glucase peptidases; and 0 to 10% of peptichainases.

After the sterilization step, the sterilization material may be adjusted to a suitable form for preparing a desired dosage form of a herbal medicine by conventional means such as, concentration in vacuum, and spray drying etc.

The desired dosage forms depend on the herbal medicines which are produced. Different herbal medicines may have different dosage forms, and a herbal medicines may have various conventional dosage forms to meet different types of therapeutically methods.

According to the present t invention, each of the herbal medicines prepared by the process of the present invention may be used in combination of one or more physiological acceptable excipients and/or auxiliaries to give formulations or compositions for various medical applications. A composition or formulation of the present invention comprises an effective amount of one of the herbal medicines of the present invention and one or more physiological acceptable excipients and or auxiliaries. The excipients and/or auxiliaries are conventional and known to the person skilled in the art.

Raw material which may be processed by using the present invention for preparing herbal medicines, are all these raw materials which has been used as raw material for preparing herbal medicines in conventional methods. For example, animals such as insects, aquatic animals and terrestrial animals; plants such as terrestrial plants and aquatic plants; and minerals such as metal salts, metal oxides and nonmetal oxides; etc.

The following examples will further illustrate the present invention and all the percentages used in the text are on the basis of weight unless otherwise indicated.

The herbal medicines can be in the preparation forms for oral, rectal parenteral, transdermal and topical administration. Forms for oral administration include, for example, tablets, coated tablets, capsules, medicines to be taken after being mixed with boiling water, wine, etc. pellets, and powder and for rectal administration include suppositories.

Topical forms include solutions, lotions, creams, ointments, powders and other conventional forms for the application of the herbal medicines to the skin.

For parenteral administration, the herbal medicines is administrated by either intravenous or intramuscular injection.

According to the present invention, a herbal medicine is prepared by the process of the present invention in which a multi-enzyme system is used to treat raw materials in order to transfer high moleculer materials into low moleculer materials.

By using the process of the present invention. Liquorice soft extract and liquorice polyssacharose are prepared from licorice roots. According to the present invention. Liquorice soft extract or liquorice polysaccharose is used for the inhibition and/or curing of diseases such as gastrointestinal disease and tumors. And they are also used for lowering the level of blood sugar, blood-lipid or serum cholesterol, increasing the rate of HDL (High Density Lipoprotein) and improving the functions of cardio-cerebral blood vessel.

For oral administration, the herbal medicine is administrated in the range of 2 to 20 mg per kilogram of body weight per day and the daily dose is divided into four individual doses.

For injection administration, the herbal medicine is administrated in the range of 0.1 to 0.5 mg per kilogram of body weight per day and the daily dose is divided into two individual doses.

Embodiment I

Preparation of liquorice soft extract and liquorice polysaccharose from Licorice Root. 100 Kg of licorice root was cracked to an average particle size of about 100 meshes. The particles were soaked for about 24 hours and were finely ground to a size of about 5 μm. 0.5 g enzymes were added which comprise 35% of cellulase, 12% of protease, 40% of amylase, 3% of lipase, 5% of lysozyme and 5% of glucase peptidase and have a specific activity concentration of 2 IU/g substrate. The enzyme treatment was done for about 5 hours. The material was filtered and the filtrate was concentrated to form liquorice soft extract. The yield of licorice acid is about 90 to 99%. The residue of the filtration was added with water and finely ground to an average size of about 10 μm or below. 12g of the same enzymes were added to adjust the specific activity concentration to 50 IU/g substrate. The enzyme treatment was done at about 65° C. for about 10 hours. After the enzyme treatment, the material was second finely ground again and then filtered to remove the residue. The filtrate was concentrated at a low temperature of 45° C. and dried by spray to form liquorice polysaccharose (oligosaccharide) The product has solubility of 100%. The residue rate is about 1 to 3% (dry weight).

Clinical practice proved that the liquorice polysaccharose produced according to the present Examples has inhibitive and curative effect to enterogastric diseases and oncoma. When the dose of oral administration is 200~2000 mg/day, it can effectively decrease the level of blood sugar, blood-lipid and blood cholesterol, increase the ratio of HDL (High Density Lipoprotein) and improve functions of cardio-cerebral blood vessels. The herbal medicine may also effectively inhibit AIDS virus and inhence the immunological competence of patients.

According to the present invention, a herbal medicine is prepared by the process of the present invention, which comprises 10–40% of mahonia stem, 10–40% of siegesbeckia herb, ~45% of speranskia tuberculate and 5–30% of cnidium fruit. The herbal medicine is used for the treatment of rheumatism (AS/RS) such as rheumatic arthritis, rhemnatoid arthritis, hyperosteogeny, osteocutanneous inflammation, cervical vertabra disease, rheumatic heart disease, lupus erythematosus, cervical vertabra disease and cor pulmonale, etc.

For oral administration, the herbal medicine is administrated in the range of 25 to 60 mg per kilogram of body weight per day the daily dose is divided into four individual doses.

For injection administration, the herbal medicine is administrated in the range of 2 to 4 mg per kilogram of body weight per day and the daily dose is divided into individual doses.

Embodiment II-1

10 Kg of mahonia stem, 20 Kg of siegesbeckia herb, 15 Kg of speranskia tuberculate and 5 Kg of cnidium fruit were mixed and cracked into particles with an average sizes of 600 meshes. The particles were soaked for 12 to 24 hours, and then were first finely ground to an average sizes of 10 μm or below. 10 g of enzymes were added to treat, with a specific activity concentration of 125 IU/g substrate, the ground material with stirring at 50° C. for 72 hours. The enzymes comprised 60% of cellulase, 15% of protease, 10% of amylase, 5% of lipase, 5% of lysozymes and 5% of peptichainase. After the enzyme treatment, the material was finely ground again. The ground mash may either directly be formulated to pellets, capsules or tablets be formulated to ointment or lotion or bath solution for the applications to skin.

Embodiment II-2

The ground mash after the enzyme treatment from Embodiment II-1 was filtered and the filtrate was then sterilized at a temperature of 50° C. The residuce rate was 6~10%. After the sterilization, the material may be formulated for the applications of oral administration or topical administration.

Embodiment II-3

10 Kg of mahonia stem, 10 Kg of siegesbeckia, 21 Kg of speranskia tuberculate and 9 Kg of cnidium fruit were mixed and cracked into particles with an average size of 1000 meshes. The soaking and finely grinding steps were the same as the Embodiment II-1. 6 g of enzymes were added to give a specific activity concentration of 75 IU/g substrate. The enzymes were composed of 44% of cellulase, 18% of protease, 18% of amylase, 10% of lipase, 5% of lysozyme and 5% of peptichainase. The enzyme treatment was made with stirring at 30° C. for 48 hours. The material was then finely ground again. The ground mash was filtered and sterilized as the Embodiment II-2. The rate of the residue was 16%. After the sterilization the mash was concentrated and dried to form powder. The powder may be used in formulations for desired applications.

I. Method of trandermal absorption: take 8~20 g product of the herbal medicine, steeped in 50~100 ml of medical alcohol for 1~60 minutes or longer, add 20~50 liters of water at temperature lower than 45° C. to form a solution, let a patient be steeped in the solution for 20~60 minutes. The temperature of water may either be kept or not be kept the same during the treatment. The patient should be kept warm and stay away from cool blow after the steeping treatment. The patient may moderately drink wine during the treatment, and is prohibited from eating raw, cold, fatty food, meat, fish and other food that are not fresh. The effects of the treatment are as follows:

a. can effectively eliminate focus of connective tissue, make collagen tissue recover normal ability;

b. can effectively decompose and through blood or body fluid circulation remove hyperosteogeny substance, and expel harmful substance from body;

c. can effectively recover impaired functions of motor nerve and autonomic nerve;

d. the cure rate of rhematic arthritis, rheumatoid arthritis, hyperosteogeny, osteocutanneous inflammation, cervical vertabra disease, rheumatic heart disease and lupus erythematosus is above 90%, the effective rate is above 95%, the cure rate of rigor vertebra inflammation and cor pulmonale is above 70% and effective rate is above 85% (see Table 1).

TABLE 1

Summary of curative effect of clinical test human body-Method of transdermal absorption

| Group | cases | Dosage (g./day) | Duration (day) | Cure rate | Effective rate | Rate of no effect |
|---|---|---|---|---|---|---|
| Rheumatic arthritis | 1858 | 15 g | 30 | 92.4% | 97.2% | 2.8% |
| Rheumatoid arthritis | 99 | 15 g | 3 × 30 | 94.8% | 97.0% | 3.0% |
| Hyperosteogeny | 146 | 15 g | 3 × 30 | 91.8% | 95.9% | 4.1% |
| Osteocutanneous inflammation | 147 | 15 g | 30 | 95.2% | 98.6% | 1.4% |
| Cervical vertebra disease | 189 | 15 g | 3 × 30 | 90.5% | 92.6% | 7.4% |
| Rheumatic hear disease | 44 | 15 g | 30 | 97.7% | 100% | 0% |
| Lupus erythematosus | 47 | 15 g | 3 × 30 | 91.5% | 95.7% | 4.3% |
| Rigor vertebra inflammation | 113 | 2 × 15 g | 6 × 30 | 71.4% | 87.4% | 12.6% |
| Cor pulmonale | 38 | 2 × 15 g | 6 × 30 | 71.0% | 94.7% | 5.3% |

II. Method of oral medication: Each time take capsul, powder or oral liquid, containing 400~800 mg product of the herbal medicine, 4 times each day (about 30 minutes before breakfast, about 30 minutes before lunch, about 30 minutes before dinner and before sleep), take the medicine with warm water at temperature lower than 45° C. Keeping warm and stay away from cool blow after the treatment. Can moderately drink wine, prohibited form eating raw, cold, fatty food, meat, fish and other food that are not fresh during the treatment. The effects of the treatment are as follows:

a. the cure rate of rheumatic arthritis, rheumatoid arthritis, hyperosteogeny, osteocutannous inflammation, cervical vertabra disease, rheumatic heart disease and lupus erythematosus is above 80%, effective rate is above 95%.

b. the cure rate of rigor vertebra inflammation and cor pulmonale is above 60% and effective rate is above 80% (see Table 2).

TABLE 2

Summary of curative effects of clinical tests on human body orally.

| Group | Cases | Dosage (mg./per time) | Number of times (day) | Duration (day) | Cure rate | Effective rate | Rate of no effect |
|---|---|---|---|---|---|---|---|
| Rheumatic arthritis | 253 | 400 | 4 | 30 | 96.4% | 100% | 0% |
| Rheumatoid arthritis | 443 | 400 | 4 | 3 × 30 | 92.3% | 95.5% | 4.5% |
| Hyperosteogeny | 387 | 400 | 4 | 3 × 30 | 82.5% | 95.4% | 4.6% |
| Osteocutanneous inflammation | 564 | 400 | 4 | 30 | 97.6% | 100% | 0% |
| Rigor vertebra inflammation | 221 | 400 | 4 | 3 × 30 | 80.1% | 96.4% | 3.6% |
| Rheumatic heart disease | 37 | 400 | 4 | 30 | 99.3% | 100% | 0% |
| Lupus erythematosus | 61 | 600 | 4 | 3 × 30 | 91.8% | 100% | 0% |
| Rigor Vertebra inflammation | 187 | 600 | 4 | 6 × 30 | 60.4% | 98.4% | 1.6% |
| Cor pulmonale | 97 | 600 | 4 | 6 × 30 | 65.0% | 97.9% | 2.1% |

Besides, using methods of applying on skin and so on are also having some effects, but there is no cure rate.

Combining methods of transdermal absorption, oral medication and applying on skin for treatment will enhance the cure effects.

Toxicity:
a. acute toxicity: $LD_{50}$ on mise by intravenous injection is 1.0 g/kg (converted to dry powder), oral medication is 4.5 g/kg.
b. subacute toxicity: experimental result on rabbit (500±100 g) proved that there was no toxic symptom when 20 mg/kg of the drug delivered to the rectum of rabbit.

6. has a capacity to decompose spur and tuberculosis of bones and joints, make periosteal collagen tissue recover normal ability.

According to the present invention, a herbal medicine is prepared by the process of the present invention which comprises 10 to 35% of goldthread root, 10 to 35% of yellow-corktree bark, 5 to 50% of rhubarb, 5 to 40% of scutellaria root, 1 to 65% of pricklyash peel. The herbal

TABLE 3

Experimental results of feeding animals

| Group | The amount of animal | Way of deliver | Dosage (mg/kg) | Duration (day) | Weight | Diet | Result activity | Defecating | Death |
|---|---|---|---|---|---|---|---|---|---|
| Watch | 30 | Rectum | 20 | 7 | ↑ | ↑ | ↑ | — | 0 |
| Control | 10 | Rectum | 1 pill | 7 | ↑ | — | — | — | 0 |

Note: (a) Control group are fed with multivitamin b pill (100 mg/per pill)
(b) "↑" stands for increase, "—" stands for normal
c. Teratogenicity: feeding experiment on mise for 6 months, does not show toxic teratogeny symptom.

Pharmacology:
1. Antiinflammation and Bacteriostasis Aqueous solution (0.1%) outside the body can effectively inhibit staphylococcus aureus, colicine and pseudomonas aemginosa. Injecting 10% aqueous solution or alcholic solution in a dose of 0.01 g/kg into rat or white rabbit, will distinctly inhibit egg-white-like rheumatic arthritis.
2. Alkaloids Reaction Low concentration (0.0001~0.1%) will stimulate frog's heart separated from body, high concentration (>0.4%) has a little effect of inhibition; but has no effect on sciatic nerve-calf specimen, body temperature and blood sugar;
3. has an effect to inhibit the function of raising pressure of adrenalin, has a little effect for lowering blood pressure, but the effect is not related to central nerve.
4. has an antiviral effect on the XINCHENG virus, can effectively extend survival time of chicken embryo.
5. has an anti-cancer effect on ascites carcinoma and osteocarcinoma, but no haemocylolysis.

medicine is administrated for treating diseases such as bacterial dematosis, fungal dermatosis, infection of urinary system, hemorrhoid and sore, etc.

For oral administration, the herbal medicine is administrated in the range of 10 to 30 mg per kilogram body weight per day and the daily dose is divided into four individual doses.

For injection administration, the herbal medicine is administrated in the range of 0.5 to 3 mg per kilogram body weight per day and the daily dose is divided into two individual doses Toxicity:

$LD_{50}$ by oral taking on mise is 2.5 g/kg, $LD_{50}$ by injection is 1.8 g/kg, and it has no sub and teratogenic toxicity.

TABLE 4

Experimental results from feeding animals

| Group | The amount of animal | Way of deliver | Dosage (mg/kg) | Duration (day) | Weight | Diet | Result activity | Defecating | Death |
|---|---|---|---|---|---|---|---|---|---|
| Watch | 30 | Rectum | 100 | 7 | ↑ | ↑ | — | — | 0 |
| Control | 10 | Rectum | 1 pill | 7 | ↑ | — | — | — | 0 |

Note: (a) Control group are fed with multivitamin b pill (100 mg/per pill)
(b) "↑" stands for increase, "—" stands for normal, "↓" stands for decent

TABLE 5

Experimental results from injection in animals

| Group | The amount of animal | Way of deliver | Dosage (mg/kg) | Duration (day) | Weight | Diet | Result activity | Defecating | Death |
|---|---|---|---|---|---|---|---|---|---|
| Watch | 30 | Vein | 20 | 7 | ↑ | — | — | — | 0 |
| Control | 10 | Vein | 1 tube (2 ml) | 7 | ↑ | — | — | — | 0 |

Note (a) Injection water is used for control group
(b) "↑" stands for increase, "—" stands for normal, "↓" stands for decent Pharmacology:

1. Effects of antimicrobial and antiprotozoon
   (a) Bacteria The herbal medicine has a capacity of inhibiting the growth or destroying hemolytic streptococcus, meningococcus, pneumococcus, vibriocholera, bacillus anthracis, staphylococcus aureus, bacillus dysenteriae, corynebacterium diphtheria, hay bacillus, pestis, bacillus proteus, bacterium coli, typhoid bacillus, bacillus pyocyaneus, etc. The mechanism is that it can inhibit the formation composition of DNA/RNA and protein of bacteria, strengthen the engulfing ability of white cell, T lymphocyte cell and liver reticuloendothelial system.
   (b) Fungus It has a capacity of destroying various dermatomyces and also can kill leptospira;
   (c) Protozoon It has a capacity of inhibiting and destroying ameba protozoon trichomonad, leishmania donovani, trypanosome, paramecium etc.;
   (d) Virus It can inhibit XINCHENG virus, influenza virus and PRS, can enable chicken embryo cultured with XINCHENG virus to survive more than 24 hours.

2. Anti-inflammation and anti allergic reaction
   (a) It can impair zymoexciting system (SH enzyme) of mastocyte, inhibit release of anaphylactic, have an effect of remitting the hypersensitive contraction/asthma of extracorporeal/in vivo trachea and can inhibit passive cutaneous anaphylaxis and histamine reaction;
   (b) It can inhibits hypersensitive inflammation and edema, lower permeability of capillary, prevent raise form bleeding reaction caused by low atmospheric pressure 3. Antipyretic Effect It has an effect on febrile rabbit caused by physical or chemical method, but no effect on normal rabbit;

4. Effect of lowering Blood Pressure and Diuretin It has a capacity of lowering blood pressure via dilatation of blood vessel, increasing volume of blood flow, at same time speeding the excretion of urinary system;

5. Blood Sugar/Blood-lipid It has no effect on ration of serum cholesterol/total phospholipid of normal people, and can lower abnormal ratio of serum cholesterol/total phospholipid;

6. Cholagogic Effect and the Effect of Spasmolysis It can increase the volume of biliation of dog and rabbit, has a conspicuous effect of inhibiting intestinal canal, and not relating to vagus nerve;

7. Sedative Effect It can inhibit raises spontaneous activity and positive conditioned reflex, eliminate frog, cat and dog's tonic spasm symptom caused by strychnine poisoning, enable animal escape from death (orally taking 100 mg every day, can raise $LD_{50}$ by 2.5 times as much as previous.)

8. Effect of Anticancer, Antiradiation and Cellular Metabolism It can inhibit the formation of DNA/RNA of cancer cell, inhibit the growth of various tumors, have a direct destroying effect on mise's sarcoma, melanoma, mastadenoma and ascites carcinoma cell.

Clinical practice proved that the herbal medicine fro oral, injection or transdermal administration has an obvious curative effects on bacterial and fungal dermatosis, mosquito bite, poisonous bee and tussokmoth bite and various hypersensitive dermatosis caused by photosensitization, chemical and physical. Moreover it has a curative effect on hepatocarcinoma, digestive system tumor, endocrine system tumor and urinary system tumor.

TABLE 6

Results form transdermal absorption treatment to bacterial dermatosis-immersion method

| Group | Cases (person) | Dosage (g/per time) | Number of times (day) | Duration (day) | Cure rate | Curative effect Effective rate | Rate of no effect |
|---|---|---|---|---|---|---|---|
| Eczema | 570 | 15 | 1 | 7 | 97.4% | 100% | 0 |
| Pustule and running sor | 60 | 15 | 1 | 7 | 100% | 100% | 0 |
| Headsore | 39 | 15 | 1 | 7 | 87.2% | 97.4% | 2.6% |
| Acne | 105 | 15 | 1 | 7 | 84.8% | 100% | 0 |
| Bedsore | 74 | 15 | 1 | 7 | 83.8% | 100% | 0 |
| Flatwart | 43 | 15 | 1 | 7 | 72.1% | 97.7% | 2.4% |
| Sharp rheumatic wart | 47 | 15 | 1 | 2 × 7 | 95.7% | 100% | 0 |
| Milliary vesicle | 47 | 15 | 1 | 7 | 100% | 100% | 0 |
| carbuncle | 32 | 15 | 2 | 4 × 7 | 90.6% | 100% | 0 |
| Beriberi | 192 | 15 | 1 | 4 × 7 | 90.6% | 100% | 0 |
| Plica | 69 | 15 | 1 | 7 | 0 | 40.6% | 59.4% |
| Macula | 62 | 15 | 1 | 7 | 100% | 100% | 0 |
| Urticaria | 71 | 15 | 1 | 7 | 100% | 1005 | 0 |
| Pudendaitch | 204 | 15 | 1 | 7 | 92.6% | 100% | 0 |
| Skin ulcer | 87 | 15 | 1 | 7 | 100% | 100% | 0 |
| Gonorrhea | 2 | 15 | 2 | 2 × 7 | 100% | 100% | 0 |

TABLE 7

Results form transdermal absorption treatment to bacterial dermatosis-method of applying on skin

| Group | Cases | Dosage (mg/time) | Number of time (time/day) | Duration (day) | Curative Rate | Curative effect Effective Rate | Rate of no effect |
|---|---|---|---|---|---|---|---|
| Acne | 257 | | 2 | 7 | 72.8% | 100% | 0 |
| | 64 | | | | 0 | 100% | 0 |
| Eczema | 267 | | 2 | 7 | 1005 | 100% | 0 |
| Pustule and running sore | 141 | | 2 | 7 | 97.9% | 100% | 0 |
| Headsore | 94 | | 2 | 7 | 86.2% | 97.8% | 2.2% |
| Bedsore | 61 | | 2 | 7 | 96.7% | 100% | 0 |
| Flatwart | 147 | | 2 | 7 | 90.5% | 98.6% | 1.4% |
| Sharp rheumatic | 62 | | 2 | 2 × 7 | 67.7% | 100% | 0 |
| Milliary vesicle | 194 | | 2 | 2 | 100% | 100% | 0 |
| Carbuncle | 39 | | 2 | 4 × 7 | 53.8% | 100% | 0 |
| Beriberi | 264 | | 2 | 4 × 7 | 97.1% | 100% | 0 |
| Plica | 241 | | 2 | 7 | 75.9% | 1005 | 0 |
| Macula | 45 | | 2 | 7 | 100% | 100% | 0 |
| Urticaria | 42 | | 2 | 7 | 100% | 100% | 0 |
| Pudendaitch | 264 | | 2 | 7 | 100% | 100% | 0 |
| Skin ulcer | 48 | | 2 | 7 | 100% | 100% | 0 |
| Poisonous bee and tussokmoth bite | 199 | | 2 | 1 | 93.9% | 100% | 0 |

Embodiment III-I

100 Kg of goldthread root, 60 Kg of yellow-croktree bark, 50 Kg of rhubarb, 100 Kg of scutellaria root and 90 Kg of pricklyash peel were mixed and cracked into particles with an average size of 2000 meshes. The particles were soaked for 6 hours and then finely ground to an average sized of 2 μm or below. 40 g of enzymes were added to give a specific activity concentration of 800 IU/g substrate. The enzymes were composed of 36% of cellulase, 22% of protease, 32% of amylase, 1% of lipase and 9% of lysozyme. The enzyme treatment was made at 75° C. for 48 hours. After the enzyme treatment, the mash was finely ground again. The ground mash was then filtered. The filtrate was sterilized in the same way as Embodiment I-1. The sterilized mash may be formulated for different applications, such as, lotions, oniments or creams, etc. for madication of skin, and the sterilized mash may also be concentrated and dried to form a product which may be used in fomulations of tablets, capsules or bath formulation, etc.

According to the present invention, a herbal medicine, comprising 5 to 40% of flavescent sophora root, 10 to 55% of stemona root, 10 to 35% of cnidium fruit, 5 to 60% of portulaca, 10 to 40% of gentian root and 5 to 60% of goldthread root, is prepared by the process of the present invention. The herbal medicine has application for treating various itches caused by, for example, skin dry, immunity endocrine uneguililium, or physical or chemical allergy. It can also inhibit itches caused by various tumors, psoriasis and neurodermatitis.

The deliver way may be transdermal absorption, oral or injection. It can be used to cure itch caused by dry, immunity endocrine umeguililium, or physical/chemical allergy.

For oral administration, the herbal medicine is administrated in the range of 10 to 30 mg per kilogram body weight per day and the daily dose is divided into four individual doses.

For injection administration, the herbal medicine is administrated in the range of 1 to 4 mg per kilogram body weight per day and the daily dose is divided into two individual doses.

Toxicity:
a. acute toxicity: $LD_{50}$ on mise by intravenous injection is 0.15 g/kg(converted to dry powder), oral medication is 0.9 g/kg.
b. subacute toxicity: experimental result on rabbit(500±100 g)proved that there was no toxic symptom when 20 mg. of the drag delivered to the rectum of rabbit.

TABLE 8

| Group | The amount of animal | Way of deliver | Dosage (mg/kg) | Duration (day) | Weight | Diet | Result activity | Deficating | Death |
|---|---|---|---|---|---|---|---|---|---|
| Watch | 30 | Rectum | 30 | 7 | + | + | + | + | 0 |
| Control | 10 | rectum | 1 pill | 7 | + | − | − | − | 0 |

Note (a) Control group are fed with multivitamin b pill (100 mg/per pill)
(b) "+" stands for increase, "−" stands for normal
c. Teratogenicity feeding experiment on mise for 6 months does not show toxic teratogeny symptom.

c. Teratogenicity feeding experiment on mise for 6 months does not show toxic teratogeny symptom.

TABLE 9

| Group | The amount of animal | Way of deliver | Dosage (mg/kg) | Duration (day) | Weight | Diet | Result activity | Deficating | Death |
|---|---|---|---|---|---|---|---|---|---|
| Watch | 30 | Vein | 20 | 7 | ↑ | — | — | — | 0 |
| Control | 10 | Vein | 1 tube (2 ml) | 7 | ↑ | — | — | — | 0 |

Note: (a) Injection water is used for control group
(b) "↑" stands for increase, "—" stands for normal, "↓" stands for decent Pharmacology:

1. Effect of antibacterial and antiprotozoon (a) Bacteria The herbal medicine can inhibit the growth or destroy hemolytic streptococcus, emningococcus, pneumococcus, vibriocholera, bacillus anthracis, staphylococcus aureus, bacillus dysenteriae, corynebacterium diphtheria, hay bacillus, streptococcus viridans, pneumobacillus, bordetella pertussis, bacillus pestis, bruceliar, clostriddium tetani, bacillus perfringens, tubercle bacilli, bacillus, proteus, bacterium coli, typhoid bacillus, bacillus pyocyaneus, etc., the mechanism is that it can inhibit the formation of DNA/RNA and protein of bacteria, strengthen the engulfing ability of white cell, T lymphocyte cell and liver reticuloendothelial system.

(b) Fungus It has a capacity of destroying various dermatomyces and also can kill leptospira;

(c) Protozoon It can inhibit and destroy ameba protozoon, trichomonad, leishmania donovani, trypanosome, paramecium etc.;

(d) Virus It can inhibit XINCHENG virus, influenza virus and PR8, smallpox virus and rabies virus can enable chicken embryo cultured with XINCHENG virus to survive more than 20 hours. It can also inhibit various pollen viruses.

2. Anti-inflammation and anti allergic reaction (a) It can impair zymoexciting system (SH enzyme) of mastocyte, inhibit release of anaphylactin, have a effect of remitting the hypersensitive contraction/asthma of extracorporeal/in vivo trachea, can inhibit passive cutaneous anaphylaxis and histamine reaction;

(b) It can inhibit hypersensitive inflammation and edema, lower permeability of capillary, prevent mise from bleeding reaction caused by low atmospheric pressure.

(c) It can decompose the diseased skin cells, recover the wizened skin caused by physiological water lost, and improve the normal cells to hyperplasia properly.

3. Antipyretic Effect It has an effect on febrile rabbit caused by physical or chemical method, but no effect on normal rabbit.

Clinical trials show that the herbal medicine can cur itches caused by various disease except itches caused by psoriasis and tumors. The clinical trials were made by administrating the medicine on skin and the results are shown on Table 10.

TABLE 10

Summary of curative effect of clinical test on human body

| Group | Cases | Complication | Number of times | Duration (day) | Cure rate | Curative effect Effect rate |
|---|---|---|---|---|---|---|
| Itch | 419 | | 1 | 7 | 83.3% | 100% |
| | | | | 4 × 7 | 94.3% | 100% |
| | 314 | Rough skin | 1 | 4 × 7 | 79.9% | 100% |
| | 71 | Plump skin | 1 | 4 × 7 | 84.5% | 100% |
| | 397 | Cutin skin | 1 | 4 × 7 | 100% | 100% |
| | 274 | Crumbs | 1 | 4 × 7 | 100% | 100% |
| | 191 | Wizened skin | 1 | 4 × 7 | 100% | 100% |
| | 152 | Redfeacks | 1 | 7 | 100% | 100% |
| | 84 | Papule | 1 | 7 | 100% | 100% |
| | 95 | Pustule and running sore | 1 | 7 | 100% | 100% |
| | 62 | Lymphomatosis | 1 | 4 × 7 | 100% | 100% |
| | 41 | Subcutaneous purpura | 1 | 4 × 7 | 75.6% | 97.6% |

Note: Itches caused by tumors and psoriasis are no included.

Embodiment IV-1

15 Kg of flavescent sophora root, 15 Kg of stemona root, 15 Kg of cnidium fruit, 16 Kg of portulaca, 15 Kg of gentian root and 10 Kg of goldthread root were mixed and cracked into particles with an average size of 100 mashes. The particles were soaked for 24 hours and then were finely ground to form a mash having particles of an average size of 5 μm or below. 4 g of enzymes were added to give a specific activity concentration of 16 IU/g substrate. The enzymes were composed of 30% of cellulase, 25% of protease, 25% of amylase, 10% of lipase, 2% of lysozyme, 4% of glucase peptidase and 4% of peptichainase. The enzyme treatment was made with stirring at 30° C. for 90 hours. The enzyme-treated mash was finely ground again. The ground mash was filtered. The residue rate was 1.4%. The filtrate was then sterilized. The sterilized mash may be formulated for medical applications to skin. The mash may be concentrated and dried to give a product which may be used in preparation for oral or parenteral administration, such as, capsules, tablets and injections etc.

According to the present invention, a herbal medicine comprising 10 to 70% of goldenlarch bark, 5 to 50% of goldthread root, 5 to 50% of flavescent sophora root, 5 to 60% of stemona root, 5 to 60% of white cloves, 5 to 40% of pricklyash peel, 5 to 70% of oldenlandia and 5 to 30% of portulaca is prepared by the process of the present invention. The herbal medicine is administrated for treating diseases, for example, intractable itches such as, psoriasis, neurodermatitis, obstinate tinea, and viral itches such as, syphilis, gonorrhea and herpes zoster.

For oral administration, the herbal medicine is administrated in the range of 5 to 30 mg per kilogram body weight per day and the daily dose is divided into four individual doses.

For injection administration, the herbal medicine is administrated in the range of 0.5 to 5 mg per kilogram body weight per day and the daily dose is divided into two individual doses.

Toxicity:

$LD_{50}$ by oral taking on mise is 1.2 g/kg, $LD_{50}$ by injection on mise is 0.2 g/kg, and it has no sub and teratogenic toxicity.

(b) Fungus It can destroy various dermatomyces and also can kill leptospira;

(c) Protozoon It can inhibit and destroy ameba protozoon, trichomonad, leishmania donovani, trypanosome, paramecium etc.;

(d) Virus It can inhibit XINCHENG virus, influenza virus and it can also effectively inhibit hepatitis virus, such as hepatitis A, B, C, etc. and specific virus, such as, herpes zoster and syphilis etc.

2. Anti-inflammation and anti allergic reaction (a) It can impair zymoexciting system (SH enzyme) of mastocyte inhibit release of anaphylactin, have an effect of remitting the hypersensitive contraction/asthma of extracorporeal/in vivo trachea can inhibit passive cutaneous anaphylaxis and histamine reaction;

(b) It can inhibit hypersensitive inflammation and edema, lower permeability of capillary, prevent mise from bleeding reaction cause by low atmospheric pressure.

(c) It can decompose the diseased skin cells, recover the wizened skin caused by physiological water lost, and improve the normal cells to hyperplasia properly.

3. Effect of Anticancer, Antiration and Cellular Motablism
   It can inhibit the formation of DNA/RNA of cancer cell, check the growth of various tumor, have a direct destroying effect on mise's sarcoma, melanoma, mastadenoma and ascites carcinoma cell.

Clinical practice proved that using product to do medical treatment in the way described above has a obvious curative effect on vrius caused skin disease, such as psoriasis, neurodenma-titis, syphilis, gonorrhea and hypes zaster and erysipelas.

The curative effect is as follows:

TABLE 11

| | Experimental results from feeding animals | | | | | | | | |
|---|---|---|---|---|---|---|---|---|---|
| Group | The amount of animal | Way of deliver | Dosage (mg/kg) | Duration (day) | Weight | Diet | Result activity | Deficating | Death |
| Watch | 30 | Rectum | 30 | 7 | ↑ | ↑ | — | — | 0 |
| Control | 10 | rectum | 1 pill | 7 | ↑ | — | — | — | 0 |

Note (a) Control group are fed with multivitamin pill (100 mg/per pill)
(b) "↑" stands for increase, "—" stands for normal, "↓" stands for decent

TABLE 12

| | Experimental results form injection in animals | | | | | | | | |
|---|---|---|---|---|---|---|---|---|---|
| Group | The amount of animal | Way of deliver | Dosage (mg/kg) | Duration (day) | Weight | Diet | Result activity | Deficating | Death |
| Watch | 30 | Vein | 5 | 7 | + | — | — | — | 0 |
| Control | 10 | Vein | 1 tube (2 ml) | 7 | + | — | — | — | 0 |

Note: (a) Injection water is used for control group
(b) "+" stands for increase, "—" stands for normal.

Pharmacology:

1. Effects of antimicrobial and antiprotozoon (a) Bacteria The herbal medicine can inhibit the growth or destroy hemolytic streptococcus, meningococcus, pneumococcus, vibriocholera, bacillus anthracis, staphylococcus aureus, bacillus dysenteriae, corynebacterium diphtheria, hay bacillus, streptococcus viridans, pneumobacillus, bordetella pertussis, bacillus pestis, brucellar proteus, bacterium coli, typhoid bacillus, bacillus pyocyaneus, etc., the mechanism is that it can inhibit the formulation of DNA/RNA and protein of bacteria, strengthen the engulfing ability of white cell, T lymphocyte cell and liver reticuloendothelial system.

1. It effectively destroy Treponema pallidum virus, psoriasis serum factor, killing gonorrhea pathogenic bacteria and other pathogenic microorganisms.

2. It can repair traumatic epidermis and teleneuron, make subcutaneous nodes soften and disappear, and recover the normal functions of epidermis and traumatic nerves by means of clearing cells with pathologic changes and speading the proliferation of normal cells; such as function is mainly realized by improving the DNA/RNA repair operated by secretory enzymes in cells.

3. Its clinical curative rates of syphilis and gonorrhea is essentially the same as those by present Western and Chinese medical methods; in views of "retrogressive irreversible pathologic changes, it also shows higher curative rate (up to over 90%), which is an advantage over the traditional medical means"

According to the present invention, a herbal medicine comprising 10~70% of poria, 1~30% of pinellia tuber, 5~50% of pilose asiabell root, 1~50% of immature bitter orange, 5~40% of green tangerine orange peel, 1~30% of

TABLE 13

Summary of curative effect on intractable itches

| Transdermal method | Disease | Cases | Dosage (g./day) | Number of time (time/day) | Duration (day) | Cure rate | Effective rate | Rate of no effect |
|---|---|---|---|---|---|---|---|---|
| Immersion | Psoriasis | 181 | 15 g | 2 | 3 × 30 | 85.1% | 100% | 0 |
|  | Neurodermatitis | 54 | 15 g | 2 | 3 × 30 | 96.3% | 100% | 0 |
|  | Obstinate tinea | 11 | 15 g | 2 | 3 × 30 | 63.6% | 100% | 0 |
|  | Syphilis | 15 | 15 g | 2 | 3 × 7 | 100% | 100% | 0 |
|  | Gonorrhea | 21 | 15 g | 2 | 2 × 7 | 100% | 100% | 0 |
| Applying | Psoriasis | 196 |  | 2 | 3 × 30 | 37.8% | 94.3% | 5.7% |
|  | Neurodermatitis | 47 |  | 2 | 3 × 30 | 59.6% | 100% | 0 |
|  | Obstinate tinea | 48 |  | 2 | 3 × 30 | 45.8% | 95.8% | 4.2% |
| on skin | Hypes zaster and erysiplas | 28 |  | 2 | 4 | 100% | 100% | 0 |
| Oral + | Posriasis | 161 | 15 + 400 | 2 + 4 | 3 × 30 | 90.1% | 100% | 0 |
| Applying on skin | Neurodermatitis | 43 | 15 + 400 | 2 + 4 | 3 × 30 | 97.7% | 100% | 0 |

Embodiment V-I

4 Kg of goldenlarch bark, 1.5 Kg of goldthread root, 1 Kg of flavescent sophora root, 0.5 Kg of stemona root, 1.2 Kg of white cloves, 0.5 Kg of pricklyash peel, 0.8 Kg of oldenlandia and 0.5 Kg of portulaca were mixed and cracked into particles with an average size of 800 meshes. The particles were soaked for 30 hours and then finely ground to form mash having an average particle size of 10 µm or below. 0.5 g of enzymes were added to give a specific activity concentration of 6 IU/g substrate. The enzymes were composed of 40% of cellulase, 25% of protease, 25% of amylase, 3% of lipase, 4% of lysozyme, 1% of glucase peplidase and 2% of peptichainase. The enzyme treatment was made with stirring at 45° C. for 144 hours. The enzyme-treated mash was freely ground again. The ground mash was filtered and the filtrate was sterilized. The residue rate was 3~7%. The sterilized mash may be formulated to applications on skin, such as, tincture, creams or lotions etc., and the sterilized mash may be spray dried to give a product which may be used in formulations for oral administration or of bath solution.

atractylodes rhizome, 1~25% of fresh ginger, 5~40% of oldenlandia and 5~40% of lonicera japonica flower, is prepared by the process of the present invention. The herbal medicine is used for treating diseases, such as, angina and pharyngitis, cardiatitis, esophagitis, enterogastritis, gastroenter ulcer, haemorrhoids, constipation, berhia, dyspepsia gastroenterli and gastroentercancer and other various tumor affections in the system, etc.

For oral administration, the herbal medicine is administrated in the range of 10 to 40 mg per kilogram body weight per day and the daily dose is divided into four individual doses.

For injection administration, the herbal medicine is administrated in the range of 1 to 5 mg per kilogram body weight per day and the daily dose is divided into two individual doses.

Toxicity:

$LD_{50}$ by oral taking on mise is 50 g/kg, it has no up-limit and has no sub and teratogenic toxicity.

TABLE 14

| | | | | | Experimental results of animals | | | | |
|---|---|---|---|---|---|---|---|---|---|
| Group | The amount of animal | Way of deliver | Dosage (mg/kg) | Duration (day) | Result | | | | |
| | | | | | Weight | Diet | activity | Deficating | Death |
| Watch | 30 | Rectum | 30 | 7 | + | + | − | − | 0 |
| Control | 10 | Rectum | 1 pill | 7 | + | − | − | − | 0 |
| Watch | 30 | Vein | 5 | 7 | + | − | − | − | 0 |
| Control | 10 | Vein | 1 tube (2 ml) | 7 | + | − | − | − | 0 |

Note:
(a) Control group are fed with multivitamin pill (100 mg/per pill)
(b) Injection water is used for control group
(c) "+" stands for increase, "−" stands for normal.

Pharmacology:

1. Effects of antimicrobial and antiprotozoon (a) Bacteria The herbal medicine can inhibit the growth or destroy hemolytic streptococcus, meningococcus, bacillus anthracis staphylococcus aureus, bacillus dysenteriae, bacterium coli, bacillus pyocyaneus, etc., (b) Protozoon It can inhibit and destroy ameba protozoon, trichomonad, leishmania donovani, trypanosome, paramecium etc..

2. Anti-inflammation and anti allergic reaction (a) It can impair zymoexciting system (SH enzyme) of mastocyte, inhibit release of anaphylactin, and can inhibit passive anaphylaxis and histamine reaction;

3. Effect of Anticancer, Antiradiation and Cellular Motablism It can inhibit the protein synthesis of DNA/RNA of cancer and has a direct damaging effect on ascitic canceration. But it has no effect on normal cells.

4. Decompose of stone It can decompose gastroenterlith through to destroy the network of protein in gastroenterlith.

Clinical trial shows that the herbal medicine administered by oral or transdermal methods has obvious curative effects on various diseases of gastroenteric system, such as, angina and pharyngitis, cardiatitis, esophagitis, gastroenteritis, gastroenter ulcer, haemorrhoids, constipation berhia, dyspepsia, gastroenterli and gastroenter cancer, etc.

The cure rate is higher than 85%, and effective rate is higher than 97%. It has a good inhibiting and curative effects on various tumor canceration of digestive system, such as, cardia cancer, laryngocarcinoma and gastroenteric cancer, etc.. The effective rate is higher than 80%.

of enzymes were added to give a specific activity concentration of 400 IU/g substrate. The enzymes were composed of 20% of cellulase, 10% of protease, 37% of amylase, 11% of lipase, 10% of lysozyme, 4% of glucase peptidase and 8% of peptichainase. The enzyme treatment was made with stirring at 75° C. for 72 hours. The enzyme-treated mash was then finely ground again and was filtered. The residue rate was 2.4%. The filtrate was sterilized. The sterilized mash may be formulated to give oral liquid The sterilized mash may also be, after dried, prepared for various medical applications in formulations such as, pellets, capsules, tablets, powders or both formulations, etc.

According to the present invention, a herbal medicine comprising 5~50% of Chinese yam, 5~65% of pueraria root, 10~70% of poria, 5~75% of dried rehmannia root, 5~60% of wolfberry fruit, 5~50% of pollen, 5~40% of rhizoma alismatis, 1~35% of mulberry leaf, 1~50% of lotus leaf, 1~50% of atractylodes rhizome, 0~35% of cherokee rose-hep and 5~65% of black plum is prepared by the process of the present invention. The herbal medicine is used for treating diseases such as diabetes mellitus.

For oral administration, the herbal medicine is administrated in the range of 10 to 50 mg(for NIDDM patients: 10 to 30 mg, IDDM patients: 20 to 50 mg, Cancer patients: 40 to 50 mg) per kilogram body weight per day and the daily dose is divided into four individual doses.

TABLE 15

Summary of curative effect of clinical test on human body

| Way of deliver | | Cases | Dosage (mg/time) | Number of time (time/day) | Duration (day) | Curative effect Curative Rate | Effective Rate |
|---|---|---|---|---|---|---|---|
| Transdermal | Gastroenter ulcer | 293 | 15000 | 1 | 30 | 100% | 100% |
| | Gastroenteritis | 299 | 15000 | 1 | 30 | 92.4% | 100% |
| | Haemorrhoids | 151 | 15000 | 1 | 30 | 86.3% | 100% |
| | Cardiatitis | 146 | 15000 | 1 | 30 | 100% | 100% |
| | Constipation | 132 | 15000 | 1 | 30 | 100% | 100% |
| Oral | Gastroenter ulcer | 152 | 400 | 4 | 30 | 94.7% | 100% |
| Oral | Gastroenteritis | 194 | 400 | 4 | 30 | 94.7% | 100% |
| | Haemorrhoids | 67 | 400 | 4 | 30 | 91.0% | 100% |
| | Cardiatitis | 34 | 400 | 4 | 30 | 91.2% | 100% |
| | Enterolith | 57 | 400 | 4 | 30 | 100% | |
| | Constipation | 86 | 400 | 4 | 30 | 100% | |

Embodiment VI-1

20 Kg of poria, 7 Kg of pinellia tuber, 8 Kg of pilose asiabell root, 13 Kg of immature bitter orange, 10 Kg of green tangerine orange peel, 10 Kg of atractylodes rhizome, 12 Kg of fresh ginger, 10 Kg of oldenlandia and 10 Kg of lonicera japonica flower were mixed and cracked into particles with an average size of 300 mashes or below. The particles were soaked for 5 hours and finely ground to form a mash with an average particle size of 5 μm or below. 30 g For injection administration, the herbal medicine is administrated in the range of 1 to 10 mg(for NIDDM patients: 1 to 4 mg, IDDM patients: 3 to 10 mg, Cancer patients: 6 to 10 mg) per kilogram body weight per day and the daily dose is divided into two individual doses.

Toxicity:

$LD_{50}$ by oral taking on mice is 12 g/kg, $LD_{50}$ by injection is 12 g/kg, and it has no sub and teratogenic toxicity.

TABLE 16

Experimental results from feeding animals

| Group | The amount of animal | Way of deliver | Dosage (mg/kg) | Duration (day) | Result | | | | |
|---|---|---|---|---|---|---|---|---|---|
| | | | | | Weight | Diet | activily | Defecating | Death |
| Watch | 30 | Rectum | 30 | 7 | + | + | – | – | 0 |
| Control | 10 | rectum | 1 pill | 7 | – | – | – | – | 0 |

Note:
(a) Control group are fed with multivitamin pill (100 mg/per pill)
(b) "+" stands for increase, "–" stands for normal.

Note:
(a) Control group are fed with multivitamin pill (100 mg/per pill)
(b) "+" stands for increase, "–" stands for normal.

TABLE 17

Experimental results from injection in animals

| Group | The amount of animal | Way of deliver | Dosage (mg/kg) | Duration (day) | Result | | | | |
|---|---|---|---|---|---|---|---|---|---|
| | | | | | Weight | Diet | activily | Defecating | Death |
| Watch | 30 | Vein | 5 | 7 | + | – | – | – | 0 |
| Control | 10 | Vein | 1 tube (2 ml) | 7 | + | – | – | – | 0 |

Note:
(a) Injection water is used for control group
(b) "+" stands for increase, "–" stands for normal, Pharmacology:
1. Anti-inflammation and anti allergic reaction
   (a) The herbal medicine can inhibit zymoexciting system (SH enzyme) of mastocyte.
   (b) It can inhibit inflammation and edema.
   (c) It can improve cell activity of white cell, T lymphocyte cell and liver reticuloendothelial system.
2. It can improve the activity and endocrine function of liver cell, kidney cell, adrenfal gland cell, pancreas cell and pancreas islet cell, and promote the equilibrium of the secretion of adrenaline insulin, demethyl adrenaline and other physiological enzymes (hormone) to the normal conditions.
3. Effect of Anticancer, Antiradiation and Cellular Metabolism It can inhibit the synthesis of DNA/RNA of cancer cell and other genvariated cell, can accelerate the synthesis of DNA/RNA of normal cell to rehabilitate the normal organizational structure and function of paraorgan.

Clinical practice proved that using product to do medical treatment in the way of transdermal absorption or oral medication has a obvious curative effect on diebate:

1. It is not necessary to control the weight of meal and carbohydrate, but it is necessary to make sure not to take any foods which contain, such as preservative substance, antiseptic, nitrite, agricultural chemical, and other cytotoxicity food, high salt food and the food containing single/dual glucose more than 50%.
2. It has obvious and widely curative effect on the complications caused by diabetes and any other diseases of endocrine system-such as glomerulonephropathy, thyropathy, gall bladder disease, hepatic disease, prostale gland disease, pancreas disease fenoglamerulone-nephro HBP (high blood pressure), hyperglycemia, hyperlipemia, hypematremia, hyperkalemia, coronary heart disease, arteriosclerosis, retinopathy, optic nerve damage, ending neuritis movement disorder of nerves motorius or autonomic nerve, etc. The cure effect is higher than 85%.
3. After treatment about 2~4 months, the organization structure and physiological function of the pathological changed organs can be recovered to normal conditions. For example, patients can recover from glomeruli, renal pelvis, damages, nerves opticus damages and pancreas damages.
4. It can recover the organization structure of pancreas to normal conditions, equilibrium the secretion rate of insulin and other hormones, keep the blood glucose rate as normal man, and urea glucose clear.
5. According to the following method to treat and nurse NIDDm and IDDm patients, the cure effect rate is higher than 75% and effect rate reaches to 97%.

I. NIDDm patients
   a. The patients who use drugs such as dibotion, glucophage etc., without hormone agent, shall stop further using the drugs after they begin to use the herbal medicine of the present invention.
   b. The patients who use the drugs such as Dibotin, Glucophage etc. with hormone agent, can begin to decrease the dosage of the drugs in the proportion of 20% each 5~7 days from a week after they begin to use the herbal medicine of the present invention, and the patients will stop using the drugs in a month after they take the herbal medicine.
   c. The patients who use the drugs such as D860, diabinese Glyburide, Diamicron, Glutril, Glurenorm etc., can begin to decrease 20% of the dosage of the drugs, in first 5 to 7 days after they take the herbal medicine of the present invention, and drop 20% each 5 days after first decrease (in practice, the proportional is according to the rehabilitation of the secretion level of insulin).

II. IDDM patients a. The dosage of insulin would be decreased 20% within first 5~7 days after the herbal medicine is taken and then decreased 20% each 5~10 days. And no insulin will be taken after 70~10 weeks. In practice, the decreasing of the dosages may be according to the rehabilitation of the secretion of insulin of himself.

After stop using insulin, keep this dosage for 1–2 months, and then the dosage drops to 200–400 mg/time, 4 times/day after all characters of endocrine, special insulin, C-peptide, BL-GLU, U-GLU, are became normal, and the organization structure and secretion function of pancreas are shown in substantially normal conditions 6. It has supplementary theriputicl effects on diseases of endocrine system and diseases related to endocrine, such as, itch, hypertension, hyperlipemia, hyperplasia of mammary glands and canceration reproductive system.

7. Has a direct destroying effect or inhibiting effect on cancer of brain, liver, kidney, bowel and stomach, lungs and bonds etc.

enzyme treatment was made with stirring at 55° C. for 100 hours. The enzyme-treated mash was finely ground again and filtered. The residue rate was 3%. The filtrate was then sterilized. The sterilized mash may be prepared to give oral solutions. After dried, the sterilized mash may be used in formulations, such as, pellets, tablets, eapsuals, powder or immersion formulations for administration to skin by immersion method etc.

According to the present invention, a herbal medicine comprising 5~30% of oriental wormwood, 1~25% of red sage root, 1~30% of dandelion herb, 2~25% of bupleurum root, 1~20% of scutellaria root, 0~40% of oldenlandia, 0~35% of pollen, 0~30% of wolfberry fruit, 1~25% of mulberry leaf, 1~25% of rhizoma alismatis is prepared by the process of the present invention.

For oral administration, the herbal medicine is administrated in the range of 10 to 25 mg(for Cancer patients: 20 to 40 mg) per kilogram body weight per day and the daily dose is divided into four individual doses.

For injection administration, the herbal medicine is administrated in the range of 1 to 4 mg(for Cancer patients:

TABLE 18

Summary of curative effects of clinical test on human body

| Way of deliver | Group | Cases | Dosage (mg/time) | Number of time (time/day) | Duration (day) | Curative Rate | Curative effect Effective | Rate |
|---|---|---|---|---|---|---|---|---|
| Immersion | NIDDM | 64 | 15000 | 2 | 6 × 30 | 79.7% | 98.8% | 100% |
| | IDDM | 33 | 15000 | 1 | 6 × 30 | 36.4% | 87.8 | 100% |
| | Prostatitis | 54 | 15000 | 1 | 3 × 30 | 98.1% | 100% | 100% |
| | Pancreatitis | 71 | 15000 | 1 | 3 × 30 | 91.5% | 100% | 100% |
| | Cancer of endocrinium | 37 | 15000 | 2 | 3 × 30 | | 83.8% | |
| Oral | NIDDM | 116 | 600 | 4 | 6 × 30 | 83.6% | 98.3% | 99.1% |
| | IDDM | 194 | 800 | 4 | 6 × 30 | 27.9% | 95.3% | 100% |
| | Prostatitis | 67 | 400 | 4 | 3 × 30 | 84.8% | 96.2% | 100% |
| | Pancreatitis | 54 | 400 | 4 | 3 × 30 | 96.2% | 100% | 100% |
| | Cancer of endocrinium | 26 | 800 | 2 | 3 × 30 | | 80.7% | |

Note:
1. The standard of the cure case is
a. B-GLU: 3.9~6.2 mmol/L, or B-GLU < 11.0 mmol/L 2 hours after eating;
b. U-GLU: normal all time;
c. the secretion of insulin: normal;
d. the characters of diebate: disappeared;
e. the complications caused by diebate: disappeared;
f. almost all relative hormone: normal.
2. Cancers of endocrinium mean cancers of brain, liver, kidney, prostate, gland, pancreas, lung, reproductive system (including womb, mammary gland), etc.

Embodiment VII-1

11 Kg of Chinese yam, 9 Kg of pueraria root, 12 Kg of poria, 10 Kg of dried rehmannia root, 8 Kg of wolfberry fruit, 13 Kg of pollen, 6 Kg of rhizoma alismatis, 12 Kg of mulberry leaf, 6 Kg of lotus leaf, 7 Kg of atractylodes rhizome and 6 Kg of black plum were mixed and cracked into praticles with an average size of 300 mashes or below. The particles were soaked for 20 hours and finely ground to a size of 5 μm or less. 20 g of enzymes were added to give a specific activity concentration of 150 IU/g substrate. The enzymes were composed of 19% of cellulase, 22% of protease, 40% of amylase, 3% of lipase, 10% of lysozyme, 3% of glucase peptidase and 3% of peptichainase. The 3 to 8 mg) per kilogram body weight per day and the daily dose is divided into two individual doses.

Toxicity:

a. acute toxicity: $LD_{50}$ on mise by intravenous injection is 2.5 g/kg(converted to powder), oral medication is 11.0 g/kg(dried powder).

b. subacute toxicity: experimental result on rabbit(500±100 g) proved that there was no toxic symptom when 20 mg of the drug delivered to the rectum of rabbit.

c. Teratogenicity feeding experiment on mise for 6 months, does not show toxic teratogeny symptom.

TABLE 19

Experimental results of feeding and injection in animals

| Group | The amount of animal | Way of deliver | Dosage (mg/kg) | Duration (day) | Result Weight | Diet | actively | Deficating | Death |
|---|---|---|---|---|---|---|---|---|---|
| Watch A | 30 | Rectum | 20 | 7 | + | – | – | – | 0 |
| Control | 10 | rectum | 1 pill | 7 | + | – | – | – | 0 |
| Watch B | 30 | Vein | 5 | 7 | + | – | – | – | 0 |
| Control | 10 | Vein | 1 tube (2 ml) | 7 | + | – | – | – | 0 |

Note:
(a) Control group A are fed with multivitamin pill (100 mg/per pill)
(b) Injection water is used for control B
(c) "+" stands for increase, "–" stands for normal Pharmacology:
1. Effect of antibacterial and antimicrobiol
   (a) Bacteria The herbal medicine can inhibit the growth of hemolytic Streptococcus, Pneumococcus, Staphylococcus aureus, Bacillus dysentefiae, Corynebactefium diphtheria, Pneumobacillus, bovine or human tubercle Bacilli, etc.
   (b) Fungus and protozoon It can inhibit the growth of various dermatomyces and also can anaesthetize roundworm and earthworm.
   (c) Virus It can inhibit and destroy, influenza virus RP8, hepatitis B virus and E CH0 11 virus.
2. Cholagogic Effect It can increase the volume of biliation of dog and rabbit, have conspicuous effect of inhibiting intestinal canal, and not related to vagus nerve;
3. Effect to experimental hepatitis It can decrease the death rate of rabbits and mise with hepatitis caused by CCL4 poisoning; the cholagogic effect are more effective to dogs with hepatitis by poisoning than other normal dogs. It can also rehabilitate HIV-level of CCL4 poisoned rabbits or dogs to normal, and stimulate their appetite. Forthermore, it can decrease the death rate and pathologic change of hepacell to experimental animals with viral hepatitis, and improve the recreation of hepacell.
4. Antipyretic Effect It has an antipyretic effect on febrile experimental animals (such as rabbits and dogs), but no effect on normal rabbit;
5. Diuretic Effect It can increase the urinary volume of domestic rabbits with toxic hepatitis and change the urea color from yellow to clear.
6. Effect of Anticancer It can inhibit the carcinoma of hepaascites, recreate sclerotic tissues, make ascites disappear and make neophastic cakings atrophy or disappear. (The mechanisms is to check the synthesis of DNA/RNA of neophastic cells and cells with pathologic changes)
7. Other Effects After administrated 2–3 weeks, it can decrease the ratios of serum cholesterol and low density lipoprotein increase the ratio of high density lipoprotein and have protection effect oh pathologic changes of aortic arch and internal organs.

Clinical practice proved that using product to do medical treatment in the way described above has a obvious curative effect on diseases, such as, virus acute and chronic hepatitis hepatitis, hepato-genous jaundice, cirrhosis and cancer of the liver, ect.

1. After 1–3 months of administration, the negative conversion rates of HBsAg, HBeAg, anti-HBcIgM, HOV-DNA, DNA-p ect. are over 80%.
2. Hepaascites disappear after 1–3 weeks of administration.
3. The rate of recovering to normal of plasmic A/G ratio prothrombin time, r-GT and serum bilirubin are over 75%.

TABLE 20

Summary of curative effect of clinical test on human body

| Way of treatment | Disease | Number of Cases | Dosage (g./day) | time (time/day) | Duration (day) | Curative effect Cure rate | Effective rate |
|---|---|---|---|---|---|---|---|
| Immersion | Hepatitis A | 41 | 15000 | 1 | 4 × 7 | 92.6% | 100% |
| | Hepatitis B | 139 | 15000 | 1 | 3 × 30 | 82.0% | 94.2% |
| | Hepatitis E | 74 | 15000 | 1 | 3 × 30 | 90.5% | 95.9% |
| | Hepatoginous janndice | 24 | 15000 | 1 | 4 × 7 | 89.5% | 100% |
| | Cirrhosisis | 77 | 15000 | 2 | 6 × 30 | 36.4% | 84.8% |
| | Cancer of liver | 17 | 15000 | 2 | 3 × 30 | | 76.7% |
| Oral | Hepatitis A | 54 | 400 | 4 | 4 × 7 | 90.7% | 100% |
| | Hepatitis B | 213 | 400 | 4 | 3 × 30 | 83.1% | 100% |
| | Hepatitis E | 96 | 600 | 4 | 3 × 30 | 88.5% | 96.8% |
| | Hepatoginous janndice | 117 | 400 | 4 | 4 × 7 | 98.3% | 100% |
| | Cirrhosisis | 41 | 600 | 4 | 6 × 30 | 41.5% | 87.8% |
| | Cancer of liver | 49 | 800 | 4 | 3 × 30 | | 53.0% |

Note: the effective rate of cancer of the liver is the control rate only.

Embodiment VIII-1

20 Kg of oriental wormwood, 3 Kg of red sage root, 15 Kg of damdelion herb, 6 Kg of bupleurum root, 9 Kg of scutellaria root, 15 Kg of oldenlandia, 6 Kg of pollen, 6 Kg of wolfberry fruit, 8 Kg of mulberry leaf and 12 Kg of rhizoma alismatis were mixed and cracked into particles with an average size of 2000 meshes. The particles were soaked for 6 hours and finely ground to an average size of 2 μm or below. 6 g of enzymes were added to give a specific activity concentration of 8 IU/g substrate. The enzymes were composed of 29% of cellulase, 10% of protease, 45% of amylase, 2% of lipase, 8% of lysozyme, 3% of glucase peptidase and 3% of peptichainase. The enzyme treatment was made with stirring at 60° C. for 24 hours. The enzyme-treated mash was finely ground again and filtered and ultra-filtered. The residue rate was 2.2%. The filtrate was concentrated under vacuum and spray dried. The product is used in formulations for various medical applications.

According to the present invention, a herbal medicine comprising of 1~30% of tetrandra root, 1~20 % of ginseng, 5~40% of cinnamom twig, 5~30% of plaster stone, 5~30% of lotus leaf, 5~30% of mulberry leaf, 1~25% of immature bitter orange and 1~40% of Cherokee rose-hip is prepared by the process of the present invention.

For oral administration, the herbal medicine is administrated in the range of 5 to 10 mg per kilogram body weight per day and the daily dose is divided into four individual doses.

For injection administration, the herbal medicine is administrated in the range of 0.5 to 1 mg per kilogram body weight per day and the daily dose is divided into two individual doses.

Toxicity:
a. When oral administration or injection in exceptional dose (>10 g/kg), no toxic reaction occurs, except excitation and insomnia are observed.
b. No chronical teratogenic poisonousness and sub-acute poisonousness are observed.

Pharmacology:
1. Effect of antiphlogisty, analgesia and antiallergy The herbal medicine can reduce the permeability of blood vessels and decrease greatly the occurrence rate of serious shock sympton caused by holoalbumen and the death rate, have notable effect to Dutch pig histamine toxic shock; can also inhibit immune hemolysis, activate lymph node, increase weight and concentration of DNA/RNA in plasmablasts and plasmocytes, and increase the amount of such cells.
2. Effect to circulatory system It can be as hypotensor by intravenous injection, intramuscular injection or oral administration and the reduction of blood pressure can be 30~65% and last longer than 2 hours without notable changes to systole, heart rate and blood transmission; can also expand blood vessels, strengthen acetylcholine's reduction effect to blood pressure, and inhibit or relieve the blood pressure boost caused by repressing aorta.
3. Effect to striated muscle It can relax striated muscle but have no notable effect to nerve block.
4. Effect to blood It can decrease greatly contents of serum cholesterol triglyoeride and low density lipoprotein and increase the ratio of high density lipoprotein after deliver for 1–2 weeks; can make the fat accumulation in liver and heart deereass or disappear.
5. Effect to anticancer It can inhibit Einstein's ascites carcinoma cells in small mouse and ascites carcinoma cells in big mouse, block their synthesis of DNA/RNA, strengthen phagocytic ability of leukocytes, T lymphocytes and endothelium network system in liver.

Clinical practice proved that using product made by the present Embodiment to cure cardio-cerebral and blood vessel diseases, such as hypertension, hyperlipemia, coronary heart disease, arteriosclerosis etc., decrease cholesterol, triglyceride and low density lipoprotein in blood, raise the content of high density lipoprotein, adjust blood viscosity and soften blood vessels. The effective rate is over 95%.

| Patient A | blood pressure (mmHg) | plasma concentration (mPa · s) | blood test | |
|---|---|---|---|---|
| In the middle of June, 1994 | 100–120 | 2.54 | T-CHOL mmocOC/L TG 2.46 mmocOC/L β-LDL 63.8% HDL-C 0.74 mmOC/L | 8.54 |
| After 1 week from administration of the product of the present Embodiment on July 2, 1994 | 80–120 | 1.36 | T-CHOL 6.52 mmOC/L TG 1.83 mm OC/L β-LDL 58.7% HDL-C 0.98% mmOC/L | |

Embodiment IX-1

12 Kg of tetrandra root, 10 Kg of ginseng, 16 Kg of cinnamom twig, 20 Kg of plaster stone, 18 Kg of lotus leaf, 18 Kg of mulberry leaf, 8 Kg of immature bitter orange and 10 Kg of cherokee rose-hip were mixed and soaked into particles with an average size of about 1000 meshes. The particles were cracked for 6 hours and finely ground to give a mash with an average partical size of 5 μm or below. 5 g of enzymes were added to give a specific activity concentration of 8 IU/g substrate. The enzymes were composed of 27% of cellulase, 24% of protease, 15% of amylase, 10% of pectase, 15% of hemicellulase, 4% of lysozyme, 3% of gulcase peptidase and 2% of peptichainase. The enzyment treatment was carried on with stirring at 50° C. for 24 hours. The enzyme-treated mash was finely ground again and filtered and ultrafiltered. The residue rate was 3%. The filtered mash was then sterilized and was then treated by an ultrasonic method and was then concentrated and dried to give a product. The product is to be used in formulations for various medical applications.

According to the present invention, a herbal medicine comprising 5~30% of ginseng, 5~30 % of astragahis root, 5~40% of lotus leaf, 5~35% of schizonepeta and 5~25% of tetrandra root is prepared by the process of the present invention.

For oral administration, the herbal medicine is administration in the range of 10 to 30 mg per kilogram body weight per day and the daily dose is divided into four individual doses.

For injection administration, the herbal medicine is administration in the range of 1 to 2 mg per kilogram body weight per day and the daily dose is divided into two individual doses.

Embodiment X-1

10 Kg of ginseng, 10 Kg of lotus leaf, 10 Kg of schizonepeta and 10 Kg of tetrandra root were mixed and cracked into a particles with an average size of about 1200 meshes. The particles were soaked for 5 hours and finely ground to give a mash with an average partical size of 10 μm or below. 2 g of enzymes were added to give a specific activity concentration of 16 IU/g. The enzymes were composed of 10% of cellulase, 35% of protease, 15% of amylase, 10% of pectase, 15% of hemicellulase, 10% of lysozyme and 5% of glucase peptidase. The enzyme-treatment was made with stirring at 70° C. for 24 hours. The enzyme-treated mash was finely ground again, filtered and ultrafitered. The residue rate was about 2%. The filtered mash was then treated by an ultrasonic method, concentrated and dried to give a product. The product may be used in formulations for various medical applications.

Toxicity:

No adverse effects have been shown by taking a large amount for oral or injection, and no sub and teratogenic toxicity have been shown.

3. Effect to the endocrime system It has notable anti-excitability effect; can strengthen the function of thyroid and sex gland and improve internal secratation unction.

4. Effect to the metabolism a. It can improve the synthesis of DNA/RNA of normal cells;

b. It can improve blood glucose metabolism, and cause to decrease body's blood glucose by mainly improving the organ breathe, accelerating fermentation of glucose, rising the level of energy metabolism.

c. It has no effect on ratio of serum CHOL/total phospholipid of normal animal, can lower abnormal ratio of serum CHOL/T-psp.

5. Effect of Diuretin By oral or injection, it has effects diuretin, and can increase the $Na^+$ draining.

6. Effect of Fatty Deposition It can effectively decrease T-CHOL, TG, LDL contains, raise HDL rate after delivering the herbal medicine for 1–6 weeks, at same time, can reduce the fatty volume of liver, heart or under skin.

7. Effect of Anticancer, Antiradiation and Cellular Motablism It can inhibit the formation of DNA/RNA of cancer cell, check the growth of various tumor.

Clinical practice proved that using product to medical treatment in the way described above has a obvious curative effect on obesity and emaciate.

TABLE 21

Experimental results from feeding animals

| Group | The amount of animal | Way of deliver | Dosage (mg/kg) | Duration (day) | Result | | | | |
|---|---|---|---|---|---|---|---|---|---|
| | | | | | Weight | Diet | activity | Deficating | Death |
| Watch | 30 | Rectum | 30 | 7 | + | + | + | + | 0 |
| Control | 10 | rectum | 1 pill | 7 | + | − | − | − | 0 |

Note:
(a) Control group are fed with multivitamin pill (100 mg/per pill)
(b) "+" stands for increase, "−" stands for normal.

TABLE 22

Experimental results from injection in animals

| Group | The amount of animal | Way of deliver | Dosage (mg/kg) | Duration (day) | Result | | | | |
|---|---|---|---|---|---|---|---|---|---|
| | | | | | Weight | Diet | activity | Deficating | Death |
| Watch | 30 | Vein | 15 | 7 | + | + | + | − | 0 |
| Control | 10 | Vein | 1 tube (2 ml) | 7 | + | − | − | − | 0 |

Note:
(a) Injection water is used for control group
(b) "+" stands for increase, "−" stands for normal.

Pharmacology:

1. Effect to never system It can strengthen the exciting process or inhibit it, improve the activity of nerve system, anti-inhibit to the condition-inflection caused by ethanol and morphine. The anti-fatigue effect of animals is notable.

2. Disease resistance It can enhance the defend ability of body to a varity of harmful stimulation and prolong the live time of experimental animals, accelerate the rehabitation of animals.

TABLE 23

Summary of curative effect of clinical test human body

| Group | Cases (person) | Dosage (g/per time) | Number of times (day) | Duration (day) | Curative effect Cure rate | Curative effect Effective rate |
|---|---|---|---|---|---|---|
| Obesity | 72 | 400 | 4 | 6 × 7 | 94.4% | 100% |
| Emaciate | 41 | 400 | 4 | 6 × 7 | 85.4% | 100% |

Note:
(a) "Obesity" herein means that the body weight exceeds the normal by over 40‰.
(b) "Emacite" herein means that the body weight is less than the normal by over 25%, except emaciates caused by diabetes and other Chronic diseases.
(c) "Cure" herein means that the body weight recovers into the range of ±20% of the normal, and the fluctuation of body weight is less than ±5% when the administration is stopped for 6 months.
(d) "Effective" herein means that the body weight recovers over 10%, and it has no significant fluctuation ( ≦ ±5%) after the administration is stopped.

What is claimed is:

1. A process for preparing a herbal medicine comprising the steps of:

forming a mash from raw material, grinding finely the mash to make the size of average suspended particles less than 50 μm, hydrolyzing the ground material by using a multi-enzyme system, the enzyme system comprising cellulases, proteases, amylases, lipases, and lysozymes and having an activity unit of from about 20,000 to about 10,000,000 IU/g, wherein the hydrolyzing takes place at a temperature of from about 20° C. to about 80° C., and sterilizing the hydrolyzed material.

2. A process as claimed in claim 1, wherein the multi-enzyme system comprises 5–75% of cellulases, 5–50% of proteases, 5–50% of amylases, 1–20% of lipases and 1–15% of lysozyme.

3. A process as claimed in claim 2, wherein the hydrolysis takes place at temperature from about 20° C. to about 80° C. for about 5 hours to about 144 hours.

4. A process as claimed in claim 1, wherein the multi-enzyme system further comprises one or more supplementary enzymes.

5. A process as claimed in claim 1, wherein the process further comprises a step of filtering the hydrolyzed material before the sterilization step.

6. A process as claimed in claim 1, wherein the process further comprises a second finely grinding step after hydrolyzing the ground material.

7. A herbal medicine for treating diseases of humans and/or animals prepared by the process of claim 1.

8. A pharmaceutical formulation comprising an effective amount of the herbal medicine as claimed in claim 7 and a physiologically acceptable excipient and/or auxiliary.

9. A herbal medicine as claimed in claim 7, wherein the herbal medicine comprises 10–40% of mahonia stem, 10–40% of siegesbeckia herb, 5–45% of sperankia stuberculata and 5–30% of cnidium fruit.

10. A herbal medicine as claimed in claim 7, wherein the herbal medicine comprises 10–35% of goldthread root, 10–35% of yellow-corktree bark, 5–50% of rhubarb, 5–40% of scutellaria root and 1–65% of pricklyash peel.

11. A herbal medicine as claimed in claim 7, wherein the herbal medicine comprises 5–40% of flavescent sophora root, 10–55% of stemona root, 10–35% of cnidium fruit, 5–60% of portulaca, 10–40% of gentian root and 5–60% of goldthread root.

12. A herbal medicine as claimed in claim 7, wherein the herbal medicine comprises 10–70% of goldenlarch bark, 5–50% of goldthread root, 5–50% of flavescent sophora root, 5–60% of stemona root, 5–60% of white cloves, 5–40% of pricklyash peel, 5–70% of oldenlandia and 5–30% of portulaca.

13. A herbal medicine as claimed in claim 7, wherein the herbal medicine comprises 10–70% of poria, 1–30% of pinellia tuber, 5–50% of pilose asiabell root, 1–50% of immature bitter orange, 5–40% of green tangerine orange peel, 1–30% of atractylodes rhizome, 1–25% of fresh ginger, 5–40% of oldenlandia and 5–40% lonicera japonica flower.

14. A herbal medicine as claimed in claim 7, wherein the herbal medicine comprises 5–50% of Chinese yam, 5–65% of pueraria root, 10–70% of poria, 5–75% of dried rehmannia root, 5–65% of wolfberry fruit, 5–50% of pollen, 5–40% of rhizoma alismatis, 1–35% of mulberry leaf, 1–50% of lotus leaf, 1–50% of atractylodes rhizome, 0–35% of cherokee rose-hip and 5–65% of black plum.

15. A herbal medicine as claimed in claim 7, wherein the herbal medicine comprises 5–30% of oriental wormwood, 1–25% of red sage root, 1–30% of dandelion herb, 2–25% of bupleurum root, 1–20% of scutellaria root, 0–40% of oldenlandia, 0–35% of pollen, 0–30% of wolfberry fruit, 1–25% of mulberry leaf, and 1–25% of rhizoma alismatis.

16. A herbal medicine as claimed in claim 7, wherein the herbal medicine comprises 1–30% of tetrandra root, 1–20% of ginseng, 5–40% of cinnamon twig, 5–30% of plaster stone, 5–30% of lotus leaf, 5–30% of mulberry leaf, 1–25% of immature bitter orange and 1–40% of Cherokee rose-hip.

17. A herbal medicine as claimed in claim 7, wherein the herbal medicine comprises 5–30% of ginseng, 5–30% of astragahis root, 5–40% of lotus leaf, 5–35% of schizonepeta and 5–25% of tetrandra root.

* * * * *